United States Patent [19]
Blaisdell et al.

[11] 4,100,415
[45] Jul. 11, 1978

[54] MODULAR PHOTOCHEMOTHERAPY CHAMBER

[75] Inventors: Ronald G. Blaisdell, Saugus; Harold L. Hough, Beverly, both of Mass.

[73] Assignee: GTE Sylvania Incorporated, Stamford, Conn.

[21] Appl. No.: 693,029

[22] Filed: Jun. 4, 1976

[51] Int. Cl.² .............................................. A61N 5/06
[52] U.S. Cl. ..................................... 250/455; 128/371
[58] Field of Search ................... 250/439 R, 455, 504; 128/371; 313/489, 493; 4/146, 147, 160

[56] References Cited

U.S. PATENT DOCUMENTS

| | | | |
|---|---|---|---|
| 910,381 | 1/1909 | Hermann | 4/146 |
| 1,578,654 | 3/1926 | Gerdes | 128/371 |
| 2,245,837 | 6/1941 | Stoddard et al. | 250/455 |
| 2,382,939 | 8/1945 | Koch | 313/489 |
| 2,631,588 | 3/1953 | Paschell | 250/455 |
| 2,822,476 | 2/1958 | Osgood | 250/455 |
| 3,587,118 | 6/1971 | Compton | 4/146 |
| 3,987,331 | 10/1976 | Schreurs | 313/493 |

FOREIGN PATENT DOCUMENTS

| | | | |
|---|---|---|---|
| 185,391 | 11/1935 | Switzerland | 4/146 |
| 336 of | 1901 | United Kingdom | 128/371 |

*Primary Examiner*—Alfred E. Smith
*Assistant Examiner*—T. N. Grigsby
*Attorney, Agent, or Firm*—Edward J. Coleman

[57] ABSTRACT

A modular chamber construction for providing ultraviolet light irradiation within a confined space. The chamber comprises a plurality of side panel assemblies mounted on a base member and arranged to form a vertically upstanding enclosure of polygonal configuration. Two of the panels are hinged to provide doors, with the remaining panels being bolted to the base and to each other. Each of the panel assemblies contains a plurality of long, tubular fluorescent lamps and associated ballast circuits, with the lamp vertically oriented and juxtaposed to face the interior of the enclosure. A top member containing filtered ventilating fans and downwardly facing mirror configuration is bolted to the top edges of the stationary side panels by means of a peripheral flange which permits mounting by sliding the top member horizontally onto the enclosure through the door opening. Each side panel has an outer cover with top and bottom vents, and a light shield may be disposed at the upper end of each side panel to prevent direct leakage of ultraviolet light through the top vents. A removable stand with a mirror surface facing upwardly is disposed on the base member within the enclosure to elevate the subject of irradiation above the dark lower end regions of the vertically disposed lamps. One side panel contains a control unit and viewing window, with the control unit being interconnected to the ballast circuits of the other side panels by plug-in cables. The doors are magnetically latched, and an interlock switch on the top member deenergizes the lamps when the doors are opened.

15 Claims, 12 Drawing Figures

MODULAR PHOTOCHEMOTHERAPY CHAMBER

BACKGROUND OF THE INVENTION

This invention relates to irradiation apparatus and, more particularly, to a photochemotherapy chamber of improved construction.

Photochemotherapy refers to the interaction of orally administered or topically applied drug compounds and subsequently applied light radiation of selected wavelengths to produce biologic changes in the skin which are beneficial. For example, controlled exposure to long-wave ultraviolet light (UVA) in the region of 320 to 400 nanometers subsequent to oral administration of psoralens has been observed to artificially induce natural tanning of the skin of the human body. In view of clinical studies in this area, such therapy appears to have significant dermatological application with respect to the medical treatment of various skin disorders.

A critical component of the photochemotherapy procedure is, of course, the irradiation apparatus; it must safely provide the proper light radiation in an efficient yet carefully controlled manner. If extensive portions of a persons body are to be irradiated and the individual is not bedridden, an upright, enclosed chamber containing an array of lamps disposed to substantially surround a standing person with light is particularly useful in this application. Prior phototherapy chambers of this type have comprised one-piece box-type enclosures with an entrance door and top exhaust fan. A plurality of special type fluorescent lamps were vertically mounted and arranged about a central standing area, with the lamp ballasts being separately located in compartments at the rear of the enclosure. Each chamber was of a steel frame and panel construction having dimensions of the order of 40 inches × 47 inches × 92 inches and a weight was about 1500 pounds. As can readily be appreciated, these early chamber constructions represented high cost units which were relatively difficult to manufacture and install, and certainly were not adapted to high volume production.

SUMMARY OF THE INVENTION

Accordingly, it is an object of the present invention to provide an improved photochemotherapy chamber construction which is particularly adapted for ease of shipping and installation and better suited to high volume production.

These and other objects, advantages and features are attained in accordance with the invention, by employing a modular construction wherein a plurality of side panel assemblies, are removably attached to a base member and to each other to provide a polygonal enclosure. The side panel construction includes a universally applicable frame member which enhances standardization. A top member is also provided which may be horizontally positioned and removably attached to cover the enclosure. Each of the side panel assemblies contains a plurality of phototherapy lamps facing the inside of the enclosure along with associated ballast circuitry. Outer covers on each side panel include top and bottom vents to facilitate convection cooling of the ballasts and lamps. A light shield may be provided at the upper end of each panel to prevent direct light leakage from the lamps via the top vents. At least one of the side panels serves as a door with a magnetic latch, and another panel supports a control unit connected to the other side panel ballasts by plug-in cables. The top member includes ventilating fans and a reflector. A removable stand having a surrounding reflector arrangement is centered on the base member for elevating a person standing in the chamber above the dark regions at the lower end thereof. An interlock switch on a side of the member facing the door functions to deenergize the lamps when the door is opened.

By virtue of the present construction, manageable separate components of the chamber can be manufactured, packaged and shipped as separate modules, with most features of the side panel modules being standardized. Once received at a given destination, the modules may be conveyed through doorways and passages with comparative ease, without the need for special heavy lift equipment. Assembly poses no problem as it merely involves relative positioning of the modules, securing with nuts and bolts, and plugging in cables. The lamps and outer covers may also be separable components which are readily assembled when the side panel frames are secured in place. Once assembled, the chamber has a comparatively stylish and neat appearance, conveniently provides the desired controlled irradiation function in a safe manner and prevents all but minimal leakage of UVA light so as to avoid injurious exposure to persons outside the chamber and deleterious effects to surrounding room surfaces.

BRIEF DESCRIPTION OF THE DRAWINGS

This invention will be more fully described hereinafter in conjunction with the accompanying drawings, in which.

DESCRIPTION OF PREFERRED EMBODIMENT

Figure 1:
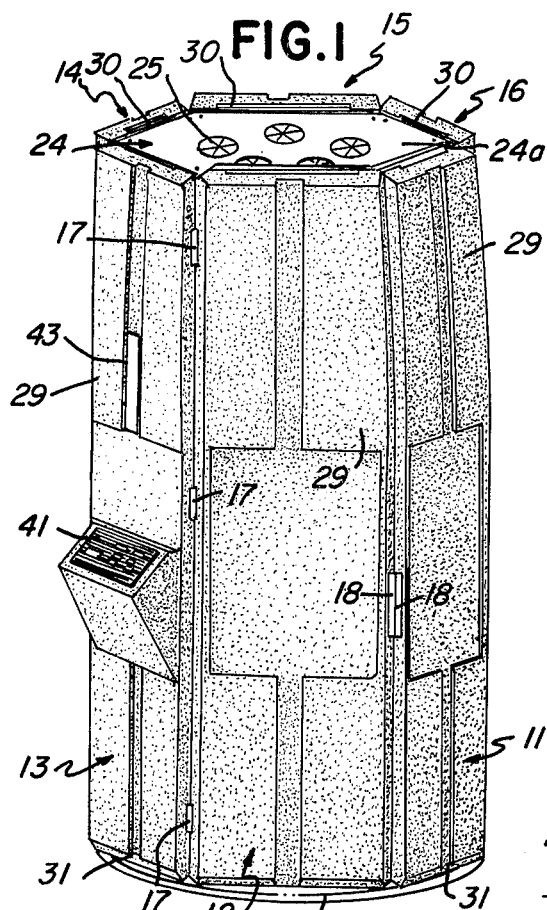
FIG. 1 is a perspective view of the chamber with the doors closed.
Figure 2:
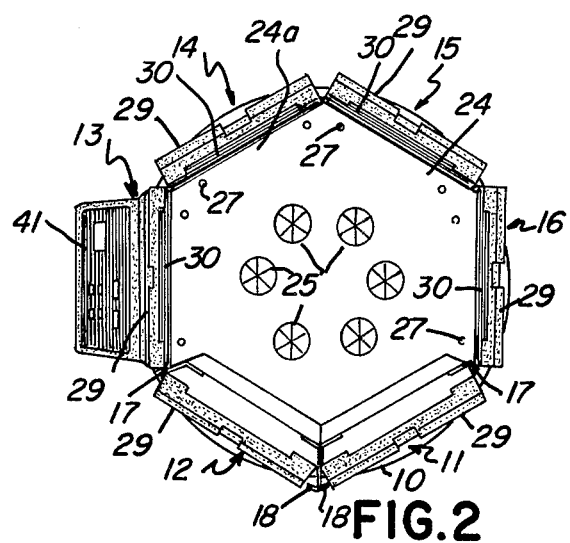
FIG. 2 is a top view of the chamber.
Figure 4:
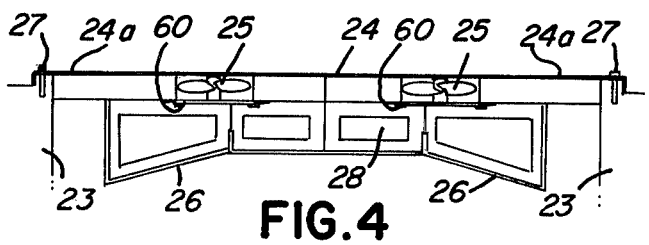
FIG. 4 is a sectional detail of the top member of the chamber.
Figure 3:
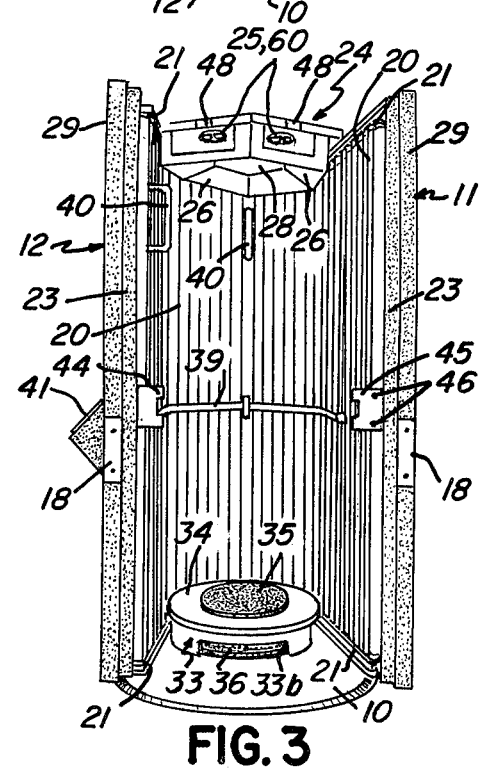
FIG. 3 is a perspective view of the chamber with the doors open to show the interior.

Referring to FIGS. 1-3, the modular photochemotherapy chamber comprises a plurality of side panel assemblies 11-16 mounted upright on a horizontal base member 10 of circular periphery and arranged to form a vertically upstanding enclosure of polygonal configuration. In the specific embodiment illustrated, six side panels are employed to form a hexagon when viewed from above (FIG. 2). Two of the side panel assemblies, namely 11 and 12, are hinged (elements 17) to provide doors having handles 18. The remaining panel assemblies 13–16 are bolted to the base 10 and to each other. More specifically, each panel assembly has two or more foot brackets 19 which are bolted to the base 10, as shown in FIG. 7, and the adjacent edges of side panel assemblies not comprising a door are bolted together, as shall be further described hereinafter.

Figure 6:
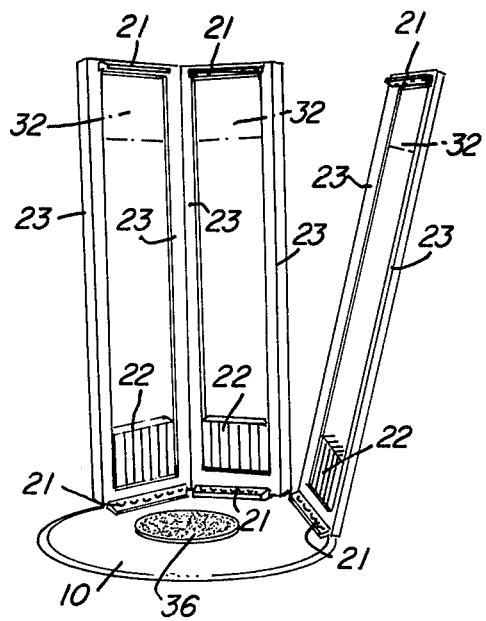
FIG. 6 is a perspective view of the side panel frames during assembly of the chamber.
Figure 7:
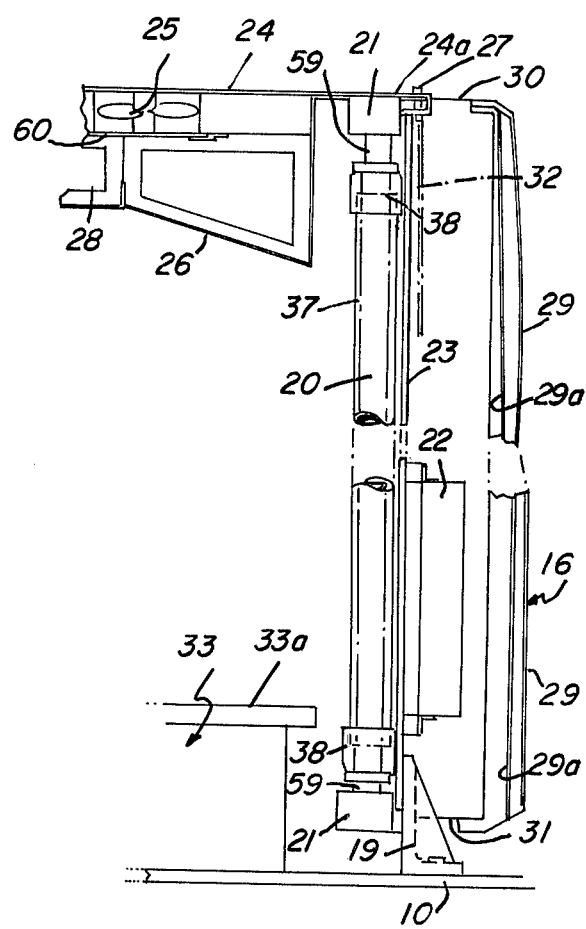
FIG. 7 is a sectional detail of a side panel assembly of the chamber, with fragmentary views of chamber portions assembled thereto.

Referring particularly to FIGS. 3 and 7, each of the side panel assemblies contains a plurality of long, tubular fluorescent lamps 20 mounted on lamp-socket brackets 21 attached at the top and bottom of each panel. The lamps are vertically oriented and juxtaposed to face the interior of the enclosure, as best shown in FIG. 3 wherein the lamps are viewed through the open doors of the chamber. Associated ballast circuits 22 for the group of lamps in each side panel assembly are mounted on the panel frame behind the lamps as viewed from the interior of the chamber. The ballast mounting is shown in FIG. 6, which illustrates the side panel frames being placed in position during assembly of the modular chamber. It will be noted from FIG. 6 that a primary support means of each side panel assembly comprises a pair of vertical frame members 23 on opposite sides thereof. As shall be described in detail, each of these frame members preferably comprises a universally applicable aluminum extrusion.

Referring to FIGS. 1–4 and 7, a top member 24 containing a plurality of ventilating fans 25 and a downwardly facing mirror configuration 26 is removably attached, such as by bolts, to the top edges of the stationary side panels 13–16 so as to cover the enclosure. The top member has a peripheral flange 24a which overlaps portions of the top ends of the stationary side panel assemblies whereby, during assembly of the chamber, the top member may be mounted on the side panel enclosure by sliding the member 24 horizontally through the door opening of the enclosure. In our preferred embodiment, the bolting down of the top member is provided by passing self-tapping screws 27 through flange 24a and into channels in frame members 23, as shall be further described hereinafter. The reflector means comprising mirror configuration 26 is suspended below the fans 25 and consists of a plurality of reflector segments arranged in a polygonal array. In the drawings, six mirror segments 26 are shown in a hexagonal array with six ventilating fans 25 disposed above the mirrors. An open central area 28, about which the mirror segments are arranged, and the spacing above the suspended mirrors provides an air channel means for ventilation. To avoid exhausting and scattering skin tissue scales outside the chamber when a person is being irradiated therein, a clip-on dust filter 60 is secured below each of the fans 25 to keep scale particles inside.

Each of the side panel assemblies further includes an outer cover 29 extending substantially the full length of the panel assembly and having both a top vent 30 and a bottom vent 31 (see FIG. 7) to facilitate convection cooling of the lamps 20 and ballast circuits 22 in each panel assembly. The outer covers 29 are preferably thermoformed of a suitable plastic material which remains stable under exposure to ultraviolet light. Alternatively, a UVA-stable material may be coated or bonded to the interior surface 29a of each cover to protect the cover material from the UVA radiation of the phototherapy lamps 20. The sides of the outer covers are attached to the vertical frame members 23, and a preferred method of accomplishing this will be described hereinafter.

In order to prevent the direct leakage of ultraviolet light through the top vents 30 of the outer covers, each panel assembly may also include a light shield 32 (a sheet of opaque material) disposed at the upper end of the panel frame, as illustrated by dashed lines in FIGS. 6 and 7. To minimize the leakage of reflected light, the interior surface 29a of each outer cover may be blackened.

A removable stand 33 with a reflecting mirror surface 34 facing upwardly is disposed on base member 10 within the enclosure to elevate the subject of irradiation above the dark lower end regions of the vertically disposed lamps 20. This feature is illustrated in FIGS. 3 and 7, where the top portion 33a of the stand 33 is shown located above the lower ends of the vertical lamps 20. The top portion 33a of stand 33 is substantially flat and has a circular resilient mat 35 centrally disposed thereon, with the reflecting mirror 34 having a generally circular configuration surrounding the mat.

Figure 5:
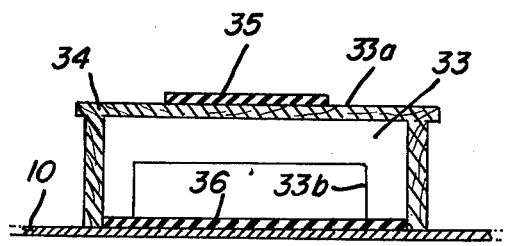
FIG. 5 is a sectional detail of the removable stand on the chamber base member.

Referring to FIGS. 3 and 5, base 10 is shown to include a disc-shaped centering means 36 upstanding from the central portion thereof. Stand 33, in turn, is shown to include an integral support portion 33b which is shaped to removably engage the centering disc 36 and, thus, retain the stand in a centered portion on the base member. In this centered position, the dimensions of the periphery of the stand provide a spacing from all of the side panel assemblies of the enclosure (see FIGS. 3 and 7).

For the protection of a person standing inside the chamber, each of the fluorescent tubes 20 is enclosed in a protective plastic sleeve 37 (see FIG. 7). Preferably there is a spacing between the glass tubing of the lamp and the enclosing sleeve 37, and the sleeve is retained by plastic end caps 38. In this manner, the lamps are protected from casual impact and, should the lamp be broken, the lamp fragments will be retained by sleeve and end cap assembly. Of course, the plastic material of which the sleeve 37 and end caps 38 are formed should be of a type which remains stable (i.e., will not discolor and disintegrate) under exposure to ultraviolet light. An extruded plastic tube 37 of "Teflon" FEP (fluorinated ethylene-propylene) has been found particularly suitable for this application, as described in U.S. Pat. No. 4,048,537 of Blaisdell et al.

Further, to guard against loss of balance within the chamber, a semicircular handrail 39 is disposed on the interior of the enclosure and attached to the side panel assemblies (FIG. 3). In the event it is desirable to provide irradiation on the undersides of a person arms or on the sides of the body, hand grips 40 are mounted on the side panel assemblies toward the upper end thereof, whereby a person within the chamber may support himself in a position with his arms extended above his shoulders.

Figure 8:
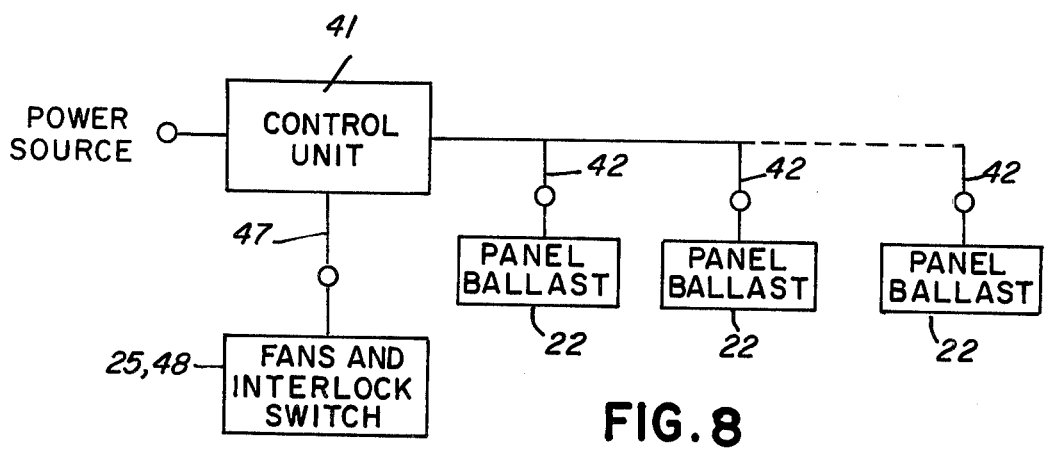
FIG. 8 is a schematic block diagram of the chamber circuitry.

A control unit 41 is mounted on the exterior of side panel assembly 13 for enabling an operator to control energization of the ballast circuits and lamps and the ventilating fans. For example, the unit may include a key-lock switch and elapsed time indicators and automatic shut-off controls to limit irradiation exposure time. As illustrated in the schematic block diagram of FIG. 8, the control unit is electrically connected to a power source and, by means of respective plug-in cables 42, to the ballast circuits 22 of each of the side panel assemblies 11–16. Of course, the unit may be directly connected to the ballast of side panel 13, upon which it is mounted. As shown in FIG. 1, a window 43 is also provided on side panel 13 for enabling an operator of the control unit to view the interior of the enclosure.

In order to facilitate entry to and exit from the chamber, the two door panels 11 and 12 further include magnetic latch means for retaining the doors in a closed position when the door panel assemblies are swung together against one another. More specifically, referring to FIGS. 3 and 4, metal brackets 44 and 45 are provided on the outer edges of the door which abut on closing, and a set of magnets 46 are inserted in the outer face of bracket 45. Hence, when the doors are closed and brackets 44 and 45 abut, the magnetic attraction between magnets 46 and metal bracket 44 provides a latching function.

A plug-in cable 47 electrically connects the power source via control unit 41 to the electrical circuits of the top member 24 including ventilating fans 25 and a set of door interlock switches 48. As shown in FIGS. 3, the interlock switches 48 are located on the front edges of the top member. Upon closing of the doors 11 and 12, the spring loaded switches 48 are depressed to permit energization of the phototherapy lamps, and upon opening the doors of the chamber, the interlock switches cause deenergization of all the lamps of the chamber. In this manner, inadvertent irradiation outside the enclosure is prevented.

Figure 9:
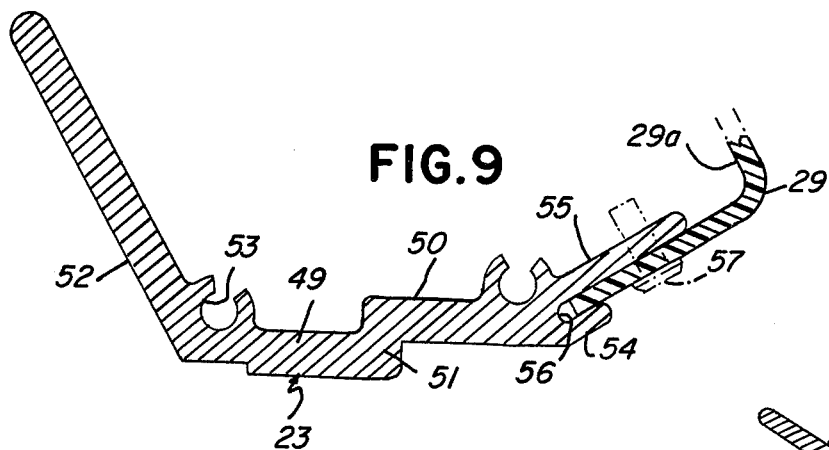
FIG. 9 is a horizontal cross-section of a vertical frame member of the chamber showing the attachment of an outer panel cover.

According to another aspect of the invention, the pair of vertical frame members 23 disposed on opposite sides of each of the side panel assemblies 11–16 are formed, such as by extrusion, to have a unique, universally applicable cross-section, as illustrated in FIG. 9. That is, each frame member 23 has the same horizontal cross-section comprising: a first linear portion 49, a second linear portion 50 offset from linear portion 49 in a plane parallel thereto, a transverse portion 51 joining the first and second linear portions, a third linear portion 52 joined at an angle to portion 49 at an end opposite that joined to the transverse portion, a circular channel 53 disposed at the inner junction of portions 49 and 52, and a parallel set of fourth and fifth linear portions 54 and 55 projecting at an angle from portion 50 at an end opposite that joined to the transverse portion. Portions 54 and 55 are spaced apart to provide a notch 56 therebetween, and portion 55 is substantially longer than portion 54. The outer cover 29 of each of the side panel assemblies has side edges which fit into the notches 56, as illustrated in FIG. 9 with respect to the interfit of one cover edge and frame notch. Secure attachment of the cover to the frame is then provided by several spaced apart screws 57 passing through the cover edge portion and into frame portion 55. Self-tapping holes, for example, may be provided in frame portion 55 for this purpose.

Figure 10:
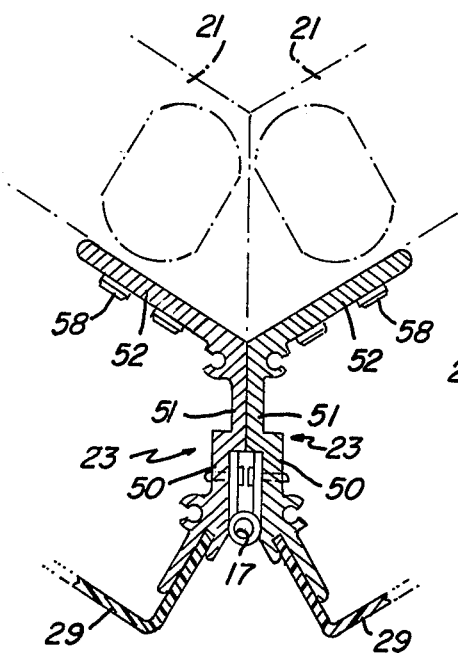
FIG. 10 is a horizontal cross-section showing two of the frame members of FIG. 9 joined by hinge and showing attachment of a lamp support bracket.

FIG. 10 shows hinges 17 attached to portions 50 of adjacent vertical frame members 23, one frame being part of the door panel assembly. FIG. 10 also shows how the lamp support bracket 21 of the panel assemblies are attached by screws or bolts 58 to portions 52 of the vertical frame.

Figure 11:
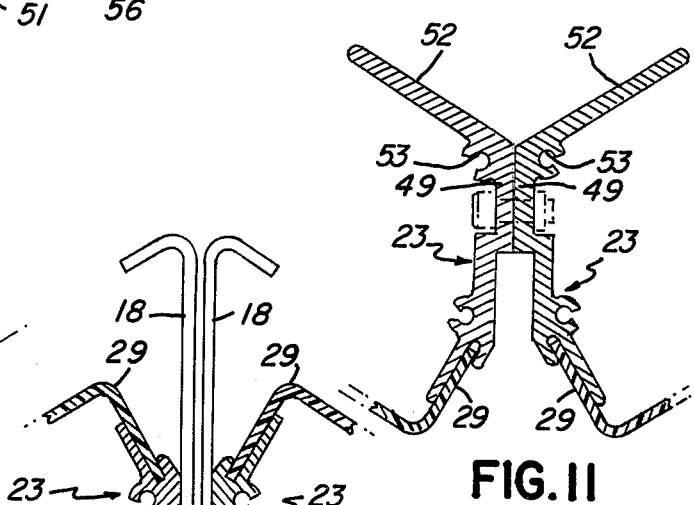
FIG. 11 is a horizontal cross-section showing two of the frame members of FIG. 9 joined by a bolt.

FIG. 11 shows a pair of adjacent vertical frame members 23 of a respectively adjacent pair of the side panel assemblies 13–16 (not comprising a door) bolted together via abutting portions 49 of the frames. Top member 24 is then attached to the upper ends of the vertical frame member 23 by self-tapping screws 27 (FIGS. 2 and 7) passing through one to member and into the circular channels 53 of the frame members (FIG. 11).

Figure 12:
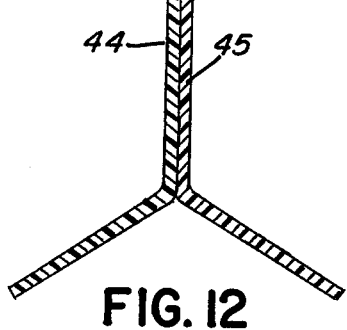
FIG. 12 is a horizontal cross-section showing two of the frame members of FIG. 9 with abutting door handles.

FIG. 12 illustrates the disposition of the door handles 18 and the brackets 44 and 45 on respective vertical frame members 23 comprising the outer edges of the door panels 11 and 12. More specifically, each handle is attached to frame portion 50 and each bracket 44, 45 is attached to frame portion 52.

According to one specific embodiment of the invention, a six-panel chamber of the type illustrated employed sixty phototherapy lamps 20 of the fluorescent tube type FR83T12 PUVA available from GTE Sylvania Incorporated. Thus, each tubular lamp had a length of about 83 inches and a diameter of about 1½ inches. Further, each fluorescent lamp 20 contained a 235° internal reflector and had shrouded single-pin bases 59 (FIG. 7) to provide proper orientation without accidental rotation due to vibration. The enclosing plastic sleeve 37 was an extruded tube of "Teflon" FEP. Each of the frame members 23 comprised an aluminum extrusion. Resilient mat 35 and centering disc 36 comprised rubber pads. The outer covers had an average thickness of about ⅛ inch and were thermoformed of ABS flame retardant plastic having a "Korad A" (Rohm and Haas) 0.003 inch UV-inhibiting liner bonded to the inside surface 29a.

Although the invention has been described with respect to a specific embodiment, it will be appreciated that modifications may be made by those skilled in the art without departing from the true spirit and scope of the invention.

What we claim is:

1. A modular photochemotherapy chamber comprising, in combination:
    a substantially horizontal base member;
    a plurality of side panel assemblies mounted vertically upright on said base member and arranged to form an enclosure;
    each of said side panel assemblies including a plurality of phototherapy lamps disposed vertically thereon and facing the inside of said enclosure, said lamps being adapted, when energized to emit substantially only ultraviolet light;
    means at one end of each of a subplurality of said side panel assemblies for removably attaching the panels to said base member;
    a substantially horizontal top member covering said enclosure and removably attached to the other end of each of said subplurality of side panel assemblies;
    at least one of said side panel assemblies not of said subplurality thereof being removably attached by hinges to an adjacent side panel assembly to thereby provide a door for said enclosure;
    means in said top member for ventilating said enclosure and
    a removable stand disposed on said base member within said enclosure and having reflector means thereon facing toward the top of said enclosure, said stand having a top portion located above the lower ends of said vertically disposed lamps.

2. The modular chamber of claim 1 wherein the top portion of said stand is substantially flat, a circular resilient mat is centrally disposed on the top portion of said stand, and said reflector means on the stand has a generally circular configuration surrounding said mat.

3. The modular chamber of claim 2 wherein said base member includes centering means upstanding therefrom, and said stand includes integral support means removably engaging said centering means whereby the stand is retained in a centered position on said base member, the dimensions of the periphery of said stand providing a spacing from all of the side panel assemblies of said enclosure when said stand is centered.

4. A modular photochemotherapy chamber comprising, in combination:
   a base member;
   a plurality of side panel assemblies mounted on said base member and arranged to form an enclosure;
   each of said side panel assemblies including a plurality of phototherapy lamps facing the inside of said enclosure;
   means at one end of each of a subplurality of said side panel assemblies for removably attaching the panels to said base member;
   a top member covering said enclosure and removably attached to the other end of each of said subplurality of side panel assemblies, said top member comprising an assembly including a ventilating fan and reflector means facing the interior of said enclosure; and
   at least one of said side panel assemblies not of said subplurality thereof being removably attached by hinges to an adjacent side panel assembly to thereby provide a door for said enclosure.

5. The modular chamber of claim 4 wherein said base and top members are substantially horizontal, said side panel assemblies are mounted vertically upright on said base member, and said top member has peripheral flange means overlapping portions of the top ends of said side panel assemblies whereby, during assembly of said chamber, said top member may be mounted on said side panel enclosure by sliding the member horizontally through the door opening of said enclosure.

6. The modular chamber of claim 5 wherein said side panel enclosure has a generally polygonal configuration when viewed from the top, each of said subplurality of panel assemblies having foot brackets bolted to said base member, the adjacent edges of side panel assemblies not comprising a door are bolted together, and the peripheral flange means of said top member is bolted to the top ends of side panel assemblies not comprising a door.

7. The modular chamber of claim 6 wherein said top member assembly includes a plurality of ventilating fans, and a dust filter secured below each of said fans, and said reflector means is suspended below said fans and comprises a plurality of reflector segments arranged in a polygonal array.

8. A modular photochemotherapy chamber comprising, in combination:
   a base member;
   a plurality of side panel assemblies mounted on said base member and arranged to form an enclosure;
   each of said side panel assemblies including a plurality of phototherapy lamps facing the inside of said enclosure and ballast circuits for said lamps;
   means at one end of each of a subplurality of said side panel assemblies for removably attaching the panels to said base member;
   a top member covering said enclosure and removably attached to the other end of each of said subplurality of side panel assemblies;
   at least one of said side panel assemblies not of said subplurality thereof being removably attached by hinges to an adjacent side panel assembly to thereby provide a door for said enclosure;
   means in said top member for ventilating said enclosure;
   a control unit mounted on the exterior of one of said side panel assemblies and electrically connected to the ballast circuits thereof; and
   plug-in cables electrically connecting said control unit to the ballast circuits of the other side panel assemblies of said enclosure, a respective plug-in cable being provided for each of said other side panel assemblies.

9. The modular chamber of claim 8 wherein the side panel assembly upon which said control unit is mounted further includes a window for enabling an operator of said control unit to view the interior of said enclosure.

10. The modular chamber of claim 8 wherein two of said side panel assemblies not of said subplurality thereof are respectively attached by hinges to adjacent side panel assemblies to thereby provide doors for said enclosure, said door panel assemblies have magnetic latch means for retaining said doors in a closed position when said door panel assemblies are swung together against one another, and said top member includes interlock switch means electrically connected to said control unit for electrically deenergizing all of the lamps of said enclosure when said doors are opened.

11. A modular photochemotherapy chamber comprising, in combination:
   a substantially horizontal base member;
   a plurality of side panel assemblies mounted vertically upright on said base member and arranged to form an enclosure;
   each of said side panel assemblies including a plurality of phototherapy lamps disposed vertically thereon and facing the inside of said enclosure, said lamps being adapted, when energized, to emit substantially only ultraviolet light;
   means at one end of each of a subplurality of said side panel assemblies for removably attaching the panels to said base member;
   each of said side panel assemblies further including ballast circuits for the lamps thereon and an outer cover extending substantially the full length of the panel assembly, said outer cover having a vent at both the top and bottom thereof to facilitate convection cooling of the lamps and ballast circuits in the panel assembly;
   a substantially horizontal top member covering said enclosure and removably attached to the other end of each of said subplurality of side panel assemblies;
   at least one of said panel assemblies not of said subplurality thereof being removably attached by hinges to an adjacent side panel assembly to thereby provide a door for said enclosure;
   means in said top member for ventilating said enclosure and
   each of said side panel assemblies further including a pair of vertical frame members on opposite sides thereof, each of said frame members having the same horizontal cross-section comprising: a first linear portion, a second linear portion offset from said first linear portion in a plane parallel thereto, a transverse portion joining said first and second linear portions, a third linear portion joined at an angle to said first portion at an end opposite that joined to the transverse portion, a circular channel disposed at the inner junction of said first and third linear portions, and a parallel set of fourth and fifth linear portions projecting at an angle from said second linear portion at an end opposite that joined to the transverse portion, said fourth and fifth portions being spaced apart to provide a notch therebetween and said fifth linear portion being substantially longer than said fourth linear portion.

12. The modular chamber of claim 11 wherein each of said vertical frame members comprises an aluminum extrusion.

13. The modular chamber of claim 11 wherein a pair of adjacent vertical frame members of adjacent ones of said side panel assemblies not comprising said door are bolted together via the abutting first linear portions thereof, and said top member is removably attached to the upper ends of said vertical frame members by self-tapping screws passing through said top member and into the circular channels of said frame members.

14. The modular chamber of claim 11 wherein each of said side panel assemblies includes lamp support means attached to the third linear portions of the vertical frame members thereof, and wherein the outer cover of each of said side panel assemblies has side edges fitting into the notches of the vertical frame members thereof and attached by screws to the fifth linear portions of said frame members.

15. The modular chamber of claim 11 wherein said hinges of said door panel assembly are attached to the second linear portions of adjacent vertical frame members.

* * * * *